(12) United States Patent
Lin et al.

(10) Patent No.: US 8,039,235 B2
(45) Date of Patent: Oct. 18, 2011

(54) OLIGONUCLEOTIDE SEQUENCES AND DNA CHIP FOR IDENTIFYING FILAMENTOUS MICROORGANISMS AND THE IDENTIFICATION METHOD THEREOF

(75) Inventors: Hui-Ling Lin, Hsinchu (TW); Teh-Ming Liang, Tainan County (TW); Tsung Chain Chang, Taoyuan County (TW); Sheng-Shung Cheng, Tainan (TW)

(73) Assignee: Industrial Technology Research Institute, Hsinchu (TW)

( * ) Notice: Subject to any disclaimer, the term of this patent is extended or adjusted under 35 U.S.C. 154(b) by 348 days.

(21) Appl. No.: 12/251,099

(22) Filed: Oct. 14, 2008

(65) Prior Publication Data

US 2009/0170103 A1 Jul. 2, 2009

(30) Foreign Application Priority Data

Dec. 26, 2007 (TW) ................................ 96150262 A

(51) Int. Cl.
*C12P 19/34* (2006.01)
*C12Q 1/68* (2006.01)

(52) U.S. Cl. ..................................... 435/91.2; 435/6.12

(58) Field of Classification Search .................. None
See application file for complete search history.

(56) References Cited

OTHER PUBLICATIONS

Patel et al., "Determination of 16S rRNA Sequences of Enterococci and Application to Species Identification of Nonmotile *Enterococcus gallinarum* Isolate," Journal of Clinical Microbiology, Nov. 1998, pp. 3399-3407, vol. 36- No. 11.

Kawamura et al., "Transfer of *Streptococcus adjacens* and *Streptococcus defectivus* to *Abiotrophia* gen. nov. as *Abiotrphia adiacens* comb. Nov. and *Abiotrophia defective* comb. nov., Respectively," International Journal of Systematic Baecteriology, Oct. 1995, pp. 798-803, vol. 45—No. 4.

Lin et al., "Use of Oligonucleotide Array for Identification of Six Foodborne Pathogens and *Pseudomonas aeruginosa* Grown on Selective Media," Journal of Food Protection, 2005,pp. 2278-2286, vol. 68- No. 11.

Tung et al., "Array-Based Indentification of Species of the Genera *Abiotrophia, Enterococcus, Granulicatella,* and *Streptococcus*," Journal of Clinical Microbiology, Dec. 2006, pp. 4414-4424, vol. 44—No. 12.

Michael Wagner, et al, "Identification and In Situ Detection of Gram-Negative Filamentous Bacteria in Activated Sludge", Systematic and Applied Microbiology, vol. 17, May 5, 1994, pp. 405-417, Taiwanese Office Action citing Wagner Article.

*Primary Examiner* — Teresa E Strzelecka
*Assistant Examiner* — Suchira Pande
(74) *Attorney, Agent, or Firm* — Muncy, Geissler, Olds & Lowe, PLLC

(57) ABSTRACT

A DNA chip for identifying filamentous microorganisms, including a substrate and a plurality of probes, wherein the probe includes SEQ ID No. 1, 2, 3, 4, 5, 6, 7, 8, 9, 10, 11, 12, 13, 14, 15, 16, complementary sequences thereof, derivatives thereof or combinations thereof. The derivative is 5' and/or 3' end of the sequence SEQ ID No. 1, 2, 3, 4, 5, 6, 7, 8, 9, 10, 11, 12, 13, 14, 15 or 16 with at least one thymidine residue added or is 5' and/or 3' end of the sequence SEQ ID No. 1, 2, 3, 4, 5, 6, 7, 8, 9, 10, 11, 12, 13, 14, 15 or 16 with one or two nucleotides added or deleted.

23 Claims, 2 Drawing Sheets

| I | II | M | XIII | XIV |
|---|---|---|---|---|
| III | IV | M | XI | XII |
| V | VI | M | IX | X |
| M | M | NC | M | M |
| XV | XVI | M | VII | VIII |
| PC | NC | M | NC | NC |

SEQUENCE LISTING

```
<160> NUMBER OF SEQ ID NOS: 33

<210> SEQ ID NO 1
<211> LENGTH: 27
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 1
aaagttatag tcatcgccct gagcgtt                                      27

<210> SEQ ID NO 2
<211> LENGTH: 28
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 2
acaaatcgtt acaaagttat agtcatcg                                     28

<210> SEQ ID NO 3
<211> LENGTH: 23
<212> TYPE: DNA
<213> ORGANISM: Artificial Sequence
<220> FEATURE:
<223> OTHER INFORMATION: Synthetic probe for identifying filamentous
      microorganisms
```

<400> SEQUENCE: 3
atttgaccct ggcctagtcc gct                                    23

<210> SEQ ID NO 4
<211> LENGTH: 23
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 4
ctagtccgct ggggttgaat cgt                                    23

<210> SEQ ID NO 5
<211> LENGTH: 21
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 5
gtctagcaag aggctggcaa t                                      21

<210> SEQ ID NO 6
<211> LENGTH: 20
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 6
attgaccgca gcggcgctat                                        20

<210> SEQ ID NO 7
<211> LENGTH: 22
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 7
tctttccagg caaaaaatac ga                                     22

<210> SEQ ID NO 8
<211> LENGTH: 22
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 8
atrtatcgac acactgttgc gt                                     22

<210> SEQ ID NO 9
<211> LENGTH: 18
<212> TYPE: DNA
<213> ORGANISM: Artificial Sequence
<220> FEATURE:
<223> OTHER INFORMATION: Synthetic probe for identifying filamentous
      microorganisms

```
<400> SEQUENCE: 9
gagttggtgg ctgggggt                                                       18

<210> SEQ ID NO 10
<211> LENGTH: 22
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 10
ttttggcgtc tacattcgta tc                                                  22

<210> SEQ ID NO 11
<211> LENGTH: 28
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 11
actgacaacc aattcgttca tcgtgtcg                                            28

<210> SEQ ID NO 12
<211> LENGTH: 22
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 12
tggctggtgc tgctgtgagt ct                                                  22

<210> SEQ ID NO 13
<211> LENGTH: 24
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 13
tgcggatgaa tgaagtaatg tcct                                                24

<210> SEQ ID NO 14
<211> LENGTH: 30
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 14
gagagtaact gagcaatcat gtatattctc                                          30

<210> SEQ ID NO 15
<211> LENGTH: 27
<212> TYPE: DNA
<213> ORGANISM: Artificial Sequence
<220> FEATURE:
<223> OTHER INFORMATION: Synthetic probe for identifying filamentous
      microorganisms
```

```
<400> SEQUENCE: 15
tgtcacgaca gagtcagaag agattgg                                          27

<210> SEQ ID NO 16
<211> LENGTH: 19
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 16
tcagtcaggt cggtgcagt                                                   19

<210> SEQ ID NO 17
<211> LENGTH: 20
<212> TYPE: DNA
<213> ORGANISM: Artificial Sequence
<220> FEATURE:
<223> OTHER INFORMATION: Synthetic position marker

<400> SEQUENCE: 17
tcctccgctt attgatatgc                                                  20

<210> SEQ ID NO 18
<211> LENGTH: 37
<212> TYPE: DNA
<213> ORGANISM: Artificial Sequence
<220> FEATURE:
<223> OTHER INFORMATION: Synthetic positive control probe

<400> SEQUENCE: 18
gggtgaagtc gtaacaaggt agccgtattt tttttt                                37

<210> SEQ ID NO 19
<211> LENGTH: 18
<212> TYPE: DNA
<213> ORGANISM: Artificial Sequence
<220> FEATURE:
<223> OTHER INFORMATION: Synthetic universal primer pair 2F

<400> SEQUENCE: 19
ttgtacacac cgcccgta                                                    18

<210> SEQ ID NO 20
<211> LENGTH: 20
<212> TYPE: DNA
<213> ORGANISM: Artificial Sequence
<220> FEATURE:
<223> OTHER INFORMATION: Synthetic universal primer pair 10R

<400> SEQUENCE: 20
ttcgcctttc cctcacggta                                                  20

<210> SEQ ID NO 21
<211> LENGTH: 16
<212> TYPE: DNA
<213> ORGANISM: Artificial Sequence
<220> FEATURE:
<223> OTHER INFORMATION: Synthetic primer M13F

<400> SEQUENCE: 21
gtaaaacgac ggccag                                                      16
```

```
<210> SEQ ID NO 22
<211> LENGTH: 17
<212> TYPE: DNA
<213> ORGANISM: Artificial Sequence
<220> FEATURE:
<223> OTHER INFORMATION: Synthetic primer M13R

<400> SEQUENCE: 22
caggaaacag ctatgac                                                 17

<210> SEQ ID NO 23
<211> LENGTH: 30
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 23
atttgaccct ggcctagtcc gcttttttttt                                  30

<210> SEQ ID NO 24
<211> LENGTH: 30
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 24
ctagtccgct ggggttgaat cgttttttttt                                  30

<210> SEQ ID NO 25
<211> LENGTH: 30
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 25
gtctagcaag aggctggcaa tttttttttt                                   30

<210> SEQ ID NO 26
<211> LENGTH: 30
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 26
attgaccgca gcggcgctat tttttttttt                                   30

<210> SEQ ID NO 27
<211> LENGTH: 30
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 27
tctttccagg caaaaaatac gattttttttt                                  30
```

```
<210> SEQ ID NO 28
<211> LENGTH: 30
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 28
atrtatcgac acactgttgc gttttttttt                                        30

<210> SEQ ID NO 29
<211> LENGTH: 30
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 29
gagttggtgg ctgggggttt tttttttttt                                        30

<210> SEQ ID NO 30
<211> LENGTH: 30
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 30
ttttggcgtc tacattcgta tcttttttttt                                       30

<210> SEQ ID NO 31
<211> LENGTH: 31
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 31
tggctggtgc tgctgtgagt cttttttttt t                                      31

<210> SEQ ID NO 32
<211> LENGTH: 30
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 32
tgcggatgaa tgaagtaatg tccttttttt                                        30

<210> SEQ ID NO 33
<211> LENGTH: 30
<212> TYPE: DNA
<213> ORGANISM: Artificial Sequence
<220> FEATURE:
<223> OTHER INFORMATION: Synthetic probe for identifying filamentous
      microorganisms

<400> SEQUENCE: 33
tcagtcaggt cggtgcagtt tttttttttt                                        30
```

OLIGONUCLEOTIDE SEQUENCES AND DNA CHIP FOR IDENTIFYING FILAMENTOUS MICROORGANISMS AND THE IDENTIFICATION METHOD THEREOF

CROSS REFERENCE TO RELATED APPLICATIONS

This application claims priority of Taiwan Patent Application No. 96150262, filed on Dec. 26, 2007, the entirety of which is incorporated by reference herein.

INCORPORATION BY REFERENCE OF SEQUENCE LISTING

A sequence listing submitted as a text file via EFS-Web is incorporated herein by reference. The text file containing the sequence listing is named "0956-A22348-US_Seq_Listing.txt"; its date of creation is Sep. 23, 2008; and its size is 3,069 bytes.

BACKGROUND OF THE INVENTION

1. Field of the Invention

The present invention relates to identification of filamentous microorganisms, particularly to the identification of those filamentous microorganisms which cause sludge bulking during waste water treatment.

2. Description of the Related Art

Most waste water processing stations use activated sludge technology as their main bio-process. However, due to the nature of industrial waste water, the bio-process itself has some inherent problems, particularly with excess foaming and sludge bulking Sludge bulking is mainly caused by the uncontrolled growth of filamentous microorganisms which result in the structural destruction of the flocs, and in their decrease subsidence. Meanwhile, because identifying filamentous microorganisms that cause sludge bulking is a timely process, filamentous microorganisms are typically not well controlled in waste water treatment resulting in poorer water quality.

Note that by expediently identifying filamentous microorganisms which cause sludge bulking in waste water treatment, prophylaxis can be enhanced. However, in conventional activated sludge systems, the bacteria flora is very complicated and classification of bacteria causing bulking cannot be made by morphology or growth condition. Therefore, conventional identification methods have their shortcomings.

There are mainly two kinds of high throughput identification methods for microorganisms. The first one is immunoassay. Immunoassay utilizes specific antibodies to a microorganism for the identification of that particular microorganism. The second one is through detection of a target gene of the particular microorganism of interest. For example, a specific gene of certain microorganism can be detected using polymerase chain reaction (PCR) or DNA hybridization (Southern blotting). However, PCR can identify only one or a few microorganisms at a time, and multiple primers are needed to identify different microorganisms. For identification of the filamentous microorganisms which causes sludge bulking in waste water treatment, multiplex PCR or serial PCRs is required. However, multiplex PCR has some disadvantages, such as decreased PCR sensitivity (Chang et al., 2001). In addition, performing serial PCRs increases assay complexity, manpower and cost. Therefore, the application of multiplex PCR for the identification of filamentous microorganisms in waste water treatment has been limited.

Bacteria contain both highly conserved and highly variable regions of DNA. Depending on the bacteria of interest and on the region of interest, the DNA for that region will either be highly variable or highly conserved. The length of the 16S rRNA gene (16S rDNA) of all bacteria is about 1.5 Kb and typically conserved. In comparison with the 16S rDNA, the length of the 23S rRNA is about 3.0 Kb and typically more variable. Different bacteria vary to a large degree in both length and sequence of the 16S-23S ribosomal DNA intergenic spacer (ITS) region. The length of the 16S-23 S ribosomal intergenic spacer region ranged from 60 to 1529 bp, and it was proposed by Gürtler that the intergenic spacer region can be used as an identification tool of microorganisms (Gürtler and Stanisich, 1996). Except for a few bacteria, the intraspecies sequence similarities of the 16S-23S ribosomal intergenic spacer are high, but interspecies sequence similarities are low. In comparison with the 16S rDNA sequence, wherein the sequencing of the 16S rDNA usually needs to be performed twice, the 16S-23S ribosomal DNA intergenic spacer region sequence is shorter and only requires one sequencing of the 16S-23S ribosomal DNA intergenic spacer region sequence to obtain the entire sequence. The divergence between interspecies of the 16S-23S ribosomal DNA intergenic spacer region sequence is greater than that of the 16 rDNA, (the similarities of the 16 rDNA between some bacteria can be as much as and even greater than 99%). Accordingly, Kawamura and Patel considered that the 16S-23S ribosomal DNA intergenic spacer region sequence is helpful for microorganism identification (Kawamura et al., 1995; Patel et al., 1998).

The present invention relates to a new method for identifying filamentous microorganisms which causes sludge bulking in waste water treatment via use of the 16S-23S ribosomal DNA intergenic spacer sequence. The new method involves amplifying the DNA of target microorganisms using PCR, and then detecting the PCR product by oligonucleotide sequence from the 16S-23S ribosomal DNA intergenic spacer sequence which are used as probes on microarrays. Currently, only Kim (Kim et al., 2004) uses a DNA chip having oligonucleotide sequences from the 16S rDNA sequence to detect filamentous microorganisms in activated sludge. Meanwhile, the intergenic spacer region sequence (ITS) has been mainly used to identify bacteria for some pathogens in biology and medicine, such as *Entercoccus* species (Tung et al., 2006), *E. coli* (Lin et al., 2005), *Granulicatella* species (Tung et al., 2006), *Pseudomonas aeruginosa* (Lin et al., 2005), *Streptococcus* species (Tung et al., 2006), etc. The intergenic spacer region sequence has not been applied for detecting filamentous microorganisms in activated sludge.

BRIEF SUMMARY OF THE INVENTION

In a first aspect, the invention provides an oligonucleotide sequence for identifying *Leucothrix mucor*, comprising: SEQ ID No. 1, SEQ ID No. 2, the complementary sequences thereof or derivatives thereof, wherein the derivative is 5' and/or 3' end of the sequence SEQ ID No. 1 or 2 with at least one thymidine residue added or is 5' and/or 3' end of the sequence SEQ ID No. 1 or 2 with one or two nucleotides added or deleted.

In a second aspect, the invention provides an oligonucleotide sequence for identifying *Leptothrix* sp., comprising: SEQ ID No. 3, SEQ ID No. 4, the complementary sequences thereof or derivatives thereof, wherein the derivative is 5' and/or 3' end of the sequence SEQ ID No. 3 or 4 with at least one thymidine residue added or is 5' and/or 3' end of the sequence SEQ ID No. 3 or 4 with one or two nucleotides added or deleted and *Leptothrix* sp. comprises *Leptothrix* sp. LMG 9068 and *Leptothrix* sp. LMG 9069.

In a third aspect, the invention provides an oligonucleotide sequence for identifying *Haliscomenobacter hydrossis*, comprising: SEQ ID No. 5, SEQ ID No. 6, the complementary sequences thereof or derivatives thereof, wherein the derivative is 5' and/or 3' end of the sequence SEQ ID No. 5 or 6 with at least one thymidine residue added or is 5' and/or 3' end of the sequence SEQ ID No. 5 or 6 with one or two nucleotides added or deleted.

In a fourth aspect, the invention provides an oligonucleotide sequence for identifying *Nocardia* sp., comprising: SEQ ID No. 7, SEQ ID No. 8, the complementary sequences thereof or derivatives thereof, wherein the derivative is 5' and/or 3' end of the sequence SEQ ID No. 7 or 8 with at least one thymidine residue added or is 5' and/or 3' end of the sequence SEQ ID No. 7 or 8 with one or two nucleotides added or deleted and *Nocardia* sp. comprises *Nocardia* sp. BCRC 15149, *Nocardia* sp. BCRC 15708 and *Nocardia* sp. BCRC 15709.

In a fifth aspect, the invention provides an oligonucleotide sequence for identifying *Nocardia amarae*, comprising: SEQ ID No. 9, SEQ ID No. 10, the complementary sequences thereof or derivatives thereof, wherein the derivative is 5' and/or 3' end of the sequence SEQ ID No. 9 or 10 with at least one thymidine residue added or is 5' and/or 3' end of the sequence SEQ ID No. 9 or 10 with one or two nucleotides added or deleted.

In a sixth aspect, the invention provides an oligonucleotide sequence for identifying *Thiothrix* sp., comprising: SEQ ID No. 11, SEQ ID No. 12, the complementary sequences thereof or derivatives thereof, wherein the derivative is 5' and/or 3' end of the sequence SEQ ID No. 11 or 12 with at least one thymidine residue added or is 5' and/or 3' end of the sequence SEQ ID No. 11 or 12 with one or two nucleotides added or deleted and *Thiothrix* sp. comprises *Thiothrix* sp. DSM 12730.

In a seventh aspect, the invention provides an oligonucleotide sequence for identifying *Thiothrix eikelboomii*, comprising: SEQ ID No. 13, SEQ ID No. 14, the complementary sequences thereof or derivatives thereof, wherein the derivative is 5' and/or 3' end of the sequence SEQ ID No. 13 or 14 with at least one thymidine residue added or is 5' and/or 3' end of the sequence SEQ ID No. 13 or 14 with one or two nucleotides added or deleted.

In an eighth aspect, the invention provides an oligonucleotide sequence for identifying *Sphaerotilus natans*, comprising: SEQ ID No. 15, SEQ ID No. 16, the complementary sequences thereof or derivatives thereof, wherein the derivative is 5' and/or 3' end of the sequence SEQ ID No. 15 or 16 with at least one thymidine residue added or is 5' and/or 3' end of the sequence SEQ ID No. 15 or 16 with one or two nucleotides added or deleted.

The invention also provides a DNA chip for identifying filamentous microorganisms, including a substrate and a plurality of probes, wherein the probe comprises SEQ ID No. 1, 2, 3, 4, 5, 6, 7, 8, 9, 10, 11, 12, 13, 14, 15, 16, complementary sequences thereof, derivatives thereof or combinations thereof. The derivative is 5' and/or 3' end of the sequence SEQ ID No. 1, 2, 3, 4, 5, 6, 7, 8, 9, 10, 11, 12, 13, 14, 15 or 16 with at least one thymidine residue added or is 5' and/or 3' end of the sequence SEQ ID No. 1, 2, 3, 4, 5, 6, 7, 8, 9, 10, 11, 12, 13, 14, 15 or 16 with one or two nucleotides added or deleted.

The invention further provides a method for identifying filamentous microorganisms causing sludge bulking, comprising: (a) extracting a DNA having a 16S-23S ribosomal DNA intergenic spacer region sequence of a filamentous microorganism which is to be identified; (b) amplifying the 16S-23S ribosomal DNA intergenic spacer region sequence via PCR and a pair of universal primers; (c) letting the 16S-23S ribosomal DNA intergenic spacer region sequence amplified in step (b) hybridize with the DNA chip for the identification of the filamentous microorganisms mentioned above; and (d) observing which probe of the DNA chip the 16S-23S ribosomal DNA intergenic spacer region sequence amplified in step (b) is hybridized with to identify the filamentous microorganism which is to be identified.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention can be more fully understood from the detailed description given herein below and the accompanying drawings which are given by way of illustration only, and thus are not limitative of the present invention, wherein:

FIG. 1 shows the position of each probe on the DNA chip of the invention; and

DETAILED DESCRIPTION OF THE INVENTION

Figure 2:
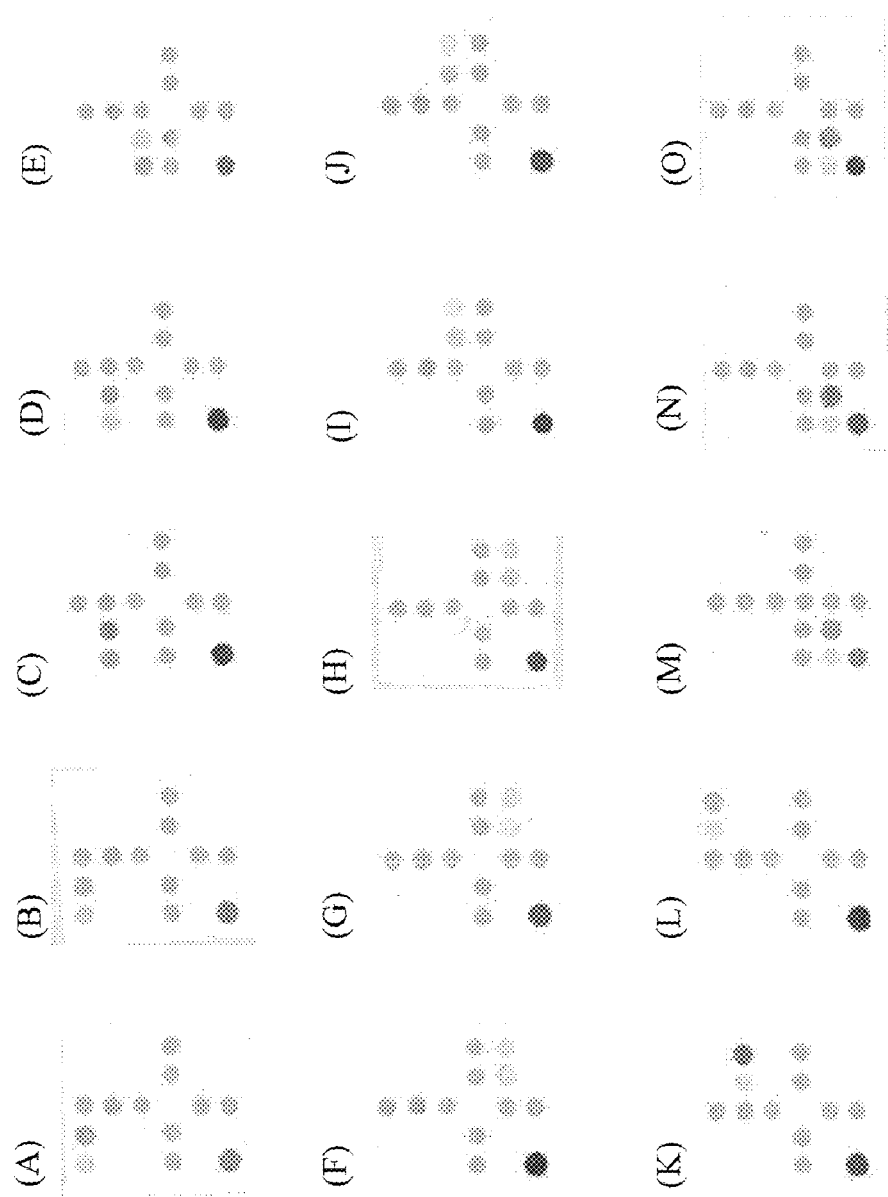
FIG. 2 (A)-(O) show the results of different bacterial strains reacting with the DNA chip of one embodiment of the invention.

The following description is of the best-contemplated mode of carrying out the invention. This description is made for the purpose of illustrating the general principles of the invention and should not be taken in a limiting sense. The invention utilizes the 16S-23S ribosomal DNA intergenic spacer region sequences of filamentous microorganisms to design specific probes for each kind of filamentous microorganisms. The probes of the invention comprise SEQ ID Nos. 1-16. The probes may be used to form a DNA chip for identifying the filamentous microorganisms causing sludge bulking, such as *Leucothrix mucor*, *Leptothrix* sp., *Haliscomenobacter hydrossis*, *Nocardia* sp., *Nocardia amarae*, *Thiothrix* sp., *Thiothrix eikelboomii* and *Sphaerotilus natans*, etc.

First, each kind of filamentous microorganism strain are collected and the 16S-23S ribosomal DNA intergenic spacer region sequences thereof are obtained from a bio-information data base (GenBank database). DNA sequencing is used for any filamentous microorganism strain for which the 16S-23S ribosomal DNA intergenic spacer region sequences could not be obtained from the bio-information data base (GenBank).

Universal primers are then used to amplify the 16S-23S ribosomal DNA intergenic spacer region sequence of the DNA of the filamentous microorganisms. The 16S-23S ribosomal DNA intergenic spacer region sequence of each filamentous microorganism is aligned by a sequence alignment software, Vector NTI (Invitrogen Corporation Carlsbead, Calif., USA), and several oligonucleotide sequence fragments having specificity and similar melting temperature (Tm) are selected for each microorganism as probes for detecting filamentous microorganisms. In addition, the complementary sequences or derivatives of the sequences selected may be used as probes. The length of the probes is about 20-30 nucleotides. Furthermore, the derivative is 5' and/or 3' ends of the selected sequences with at least one thymidine residue added or is 5' and/or 3' ends of the selected sequences with one or two nucleotides added or deleted. Note that adding at least one thymidine residue at 3' ends of the selected sequences may enhance the signal of the hybridization and the number of added thymidine residues is preferably about 5-15.

After that, the probes are dissolved in a dye liquor and spotted on a substrate to form a DNA chip by automatic arrayer (SR-A300; Ezspot, Taipei, Taiwan) by using a solid pin (diameter, 400 μm). The substrate may comprise nylon membrane, glass, cellulose nitrate membrane or plastic.

The DNA chip may further comprise a plurality of position markers, a plurality of positive control probes and a plurality of negative controls. The position marker may comprise an internal transcribed spacer 4 (ITS-4) (5' TCCTCCGCTTAT-TGATATGC 3' (SEQ ID. No. 17)) labeled with a digoxigenin (DIG). The positive control probe may comprise a sequence of 5' GGGTGAAGTCGTAACAAGGTAGCCGTAttttttttt 3' (SEQ ID. No. 18); while the negative control may contain no probes at all, comprising only of the dye liquor which is used for dissolving the probes.

The DNA of the filamentous microorganism are then extracted and used to perform a polymerase chain reaction or a nested polymerase chain reaction by universal primers for the 16S-23S ribosomal DNA intergenic spacer region sequence of bacterium to amplify the 16S-23S ribosomal DNA intergenic spacer region sequence of the filamentous microorganism which is to be identified. The universal primers used in this polymerase chain reaction have been labeled in order to produce a signal when the polymerase chain reaction product of the 16S-23S ribosomal DNA intergenic spacer region sequence hybridizes with the probes. In one embodiment, a digoxigenin is labeled at the 5' end of the primer.

The polymerase chain reaction product is heated so as to denature the double stranded product and form single strands to hybridize with the probes of the DNA chip of the invention. If the polymerase chain reaction product of the filamentous microorganism which is to be identified hybridizes with a certain probe of the DNA chip of the invention, the filamentous microorganism can be identified.

In one embodiment, by using the DNA chip of the invention, 15 filamentous microorganism strains which were the target microorganisms were correctly identified; the DNA chip thus demonstrated 100% sensitivity. Furthermore, 65 non-filamentous microorganism strains which were not the target of the DNA chip of the invention showed no hybridization signal at all; the DNA chip thus demonstrated 100% specificity. Accordingly, the probes and the DNA chip of the invention had excellent sensitivity and specificity.

Example

Collection of the Filamentous Microorganism Strains

Most of the filamentous microorganism strains collected in the invention were from the Bioresources Collection and Research Center, Taiwan (BCRC), American Type Culture Collection (ATCC), Manassa, Va., USA, Deutsche Sammlung von Mikroorganismen und Zellkulture (DSMZ) and Laboratorium voor Microbiologie Gent, Belgium (LMG).

Amplification and Sequencing of the 16S-23S Ribosomal DNA Intergenic Spacer Region Sequence of the Filamentous Microorganisms DNA of each filamentous microorganism used in the invention was extracted to perform a polymerase chain reaction in order to amplify the 16S-23S ribosomal DNA intergenic spacer region sequence of the DNA.

Polymerase Chain Reaction:

Each 50 μl of polymerase chain reaction solution contained 5 μl of template DNA, 5 μl of PCR buffer (10×), 0.15 mM of deoxyribonucleoside triphosphates (dNTP) (PROtech Technologies, Inc. PTM8014, Taipei, Taiwan), 1 μM of universal primer pair: 2F (5' TTGTACACACCGCCCGTA 3' (SEQ ID. No. 19)) and 10R (5'TTCGCCTTTCCCTCACGGTA 3' (SEQ ID. No. 20)), and 1 U of Taq polymerase (ProZyme™ II, PROtech Technologies, Inc., Taipei, Taiwan). 50 μl of mineral oil was added on each reaction solution. The polymerase chain reaction condition was: 94° C., 3 minutes; 94° C., 1 min, 55° C., 1 minute, 72° C., 1.5 minutes (35 cycles); 72° C., 7 minutes (1 cycle).

Molecular Cloning

Gel electrophoresis of the PCR products were performed in 2% agarose and 100 bp ladder was used as a marker. The gel electrophoresis was performed with 100 V voltage for 30 minutes. Then, the agarose gel was stained with ethidium bromide in sharking condition for 20 minutes and an UV light image process system (IS-2000 Digital Imaging System, Alpha Innotech Corporation, San Leandro, Calif., USA) was used to record the result image. After that, the PCR products were purified by a kit (PCR-M Clean Up System, Viogene, Taipei, Taiwan) and then sequencing of the purified PCR products was performed by ABI Prism 377 automated system (Applied Biosystems, Taipei, Taiwan).

If the PCR product of the filamentous microorganism on the electrophoresis gel was not a single band, molecular cloning of the PCR product was performed. TOPO TA Cloning Kit (Invitrogen, USA) was used for molecular cloning and the plasmid thereof was PCR 2.1-TOPO, competent cells thereof were Top10F' One Shot. The PCR product was inserted in the plasmid DNA and then the plasmid DNA was transplanted into E. coli competent cells (Top10F' One Shot). The competent cells were incubated in S.O.C. medium (from the kit) at 37° C. for 1 hour. Then the E. coli bacterium containing plasmid were applied on an LB agar plate containing kanamycin (50 μg/μl), 40 μl of IPTG (100 mM) and 40 μl of X-gal (40 mg/ml) and incubated at 37° C. for about 12-16 hours. The blue colonies meant that no plasmid was inserted. Therefore, the white colonies were picked up. Then, PCR, using a specific primer (M13F, M13R), and gel electrophoresis, were performed to further select the white colonies. After the selection, the target DNA fragment was amplified by universal primers (2F, 10R) for the target DNA fragment. The amplified target DNA fragment was then confirmed by a gel electrophoresis, and sequencing of the amplified target DNA fragment was performed. The sequences of the primers are shown in Table 1.

TABLE 1

The sequences of the primers:

| | Primers | Sequence (5'---3') | |
|---|---|---|---|
| Molecular cloning | M13F | GTAAAACGACGGCCAG (SEQ ID. No. 21) | Plasmid |
| | M13R | CAGGAAACAGCTATGAC (SEQ ID. No. 22) | Plasmid |

TABLE 1-continued

The sequences of the primers:

| Primers | | Sequence (5'---3') | |
|---|---|---|---|
| Sequencing | 2F | TTGTACACACCGCCCGTA (SEQ ID. No. 19) | Bacteria |
| | 10R | TTCGCCTTTCCCTCACGGTA (SEQ ID. No. 20) | Bacteria |

Probe Design

Alignments of the 16S-23S ribosomal DNA intergenic spacer region sequences of the filamentous microorganisms were performed by using the PrettyBox algorithm of the Wisconsin Genetics Computer Group package (version 10.3; Accelrys Inc., San Diego, Calif.) and the similarities of the 16S-23S ribosomal DNA intergenic spacer region sequences were obtained. The 16S-23S ribosomal DNA intergenic spacer region sequences of the filamentous microorganisms were aligned to the 16S-23S ribosomal DNA intergenic spacer region sequences of related or other strain or genus of bacteria, and then specific sequence in the 16S-23S ribosomal DNA intergenic spacer region sequence of each filamentous microorganism were obtained. Several oligonucleotide probes for each filamentous microorganism were designed from the 16S-23S ribosomal DNA intergenic spacer region sequence thereof. The length of the probes were about 20-30 nucleotides. The melting temperatures of the probes were similar. The obtained probes and the target filamentous microorganisms thereof are listed in Table 2.

TABLE 2

Probes and the target filamentous microorganisms thereof:

| Strains | Sequence of probes |
|---|---|
| Leucothrix mucor | SEQ ID No. 1 |
| | SEQ ID No. 2 |
| Leptothrix sp. | SEQ ID No. 3 |
| | SEQ ID No. 4 |
| Haliscomenobacter hydrossis | SEQ ID No. 5 |
| | SEQ ID No. 6 |
| Nocardia sp. | SEQ ID No. 7 |
| | SEQ ID No. 8 |
| Nocardia amarae | SEQ ID No. 9 |
| | SEQ ID No. 10 |
| Thiothrix sp. | SEQ ID No. 11 |
| | SEQ ID No. 12 |
| Thiothrix eikelboomii | SEQ ID No. 13 |
| | SEQ ID No. 14 |
| Sphaerotilus natans | SEQ ID No. 15 |
| | SEQ ID No. 16 |

Note that the probes can also be the complementary sequences and derivatives of SEQ ID Nos. 1-16. The derivative is 5' and/or 3' ends of the sequence SEQ ID Nos. 1-16 with at least one thymidine residue added to enhance the hybridization signal or is 5' and/or 3' end of the sequence SEQ ID Nos. 1-16 with one or two nucleotides added or deleted. The probes used in this example are listed in Table 3.

TABLE 3

Probes used in the example:

| Strains | Sequence of probes | Code name of probes | $T_m$ (° C.) |
|---|---|---|---|
| Leucothrix mucor | SEQ ID No. 1 | I | 60.5 |
| | SEQ ID No. 2 | II | 52.8 |

TABLE 3-continued

Probes used in the example:

| Strains | Sequence of probes | Code name of probes | $T_m$ (° C.) |
|---|---|---|---|
| Leptothrix sp. | SEQ ID No. 3 adding 7 thymidine residues at 3' end (SEQ ID No. 23) | III | 60.9 |
| | SEQ ID No. 4 adding 7 thymidine residues at 3' end (SEQ ID No. 24) | IV | 60.2 |
| Haliscomenobacter hydrossis | SEQ ID No. 5 adding 9 thymidine residues at 3' end (SEQ ID No. 25) | V | 52.9 |
| | SEQ ID No. 6 adding 10 thymidine residues at 3' end (SEQ ID No. 26) | VI | 61.4 |
| Nocardia sp. | SEQ ID No. 7 adding 8 thymidine residues at 3' end (SEQ ID No. 27) | VII | 53.4 |
| | SEQ ID No. 8 adding 8 thymidine residues at 3' end (SEQ ID No. 28) | VIII | 50.6 |
| Nocardia amarae | SEQ ID No. 9 adding 12 thymidine residues at 3' end (SEQ ID No. 29) | IX | 54.2 |
| | SEQ ID No. 10 adding 8 thymidine residues at 3' end (SEQ ID No. 30) | X | 51.4 |
| Thiothrix sp. | SEQ ID No. 11 | XI | 59.6 |
| | SEQ ID No. 12 adding 9 thymidine residues at 3' end (SEQ ID No. 31) | XII | 59.5 |
| Thiothrix eikelboomii | SEQ ID No. 13 adding 6 thymidine residues at 3' end (SEQ ID No. 32) | XIII | 56.5 |
| | SEQ ID No. 14 | XIV | 54.0 |
| Sphaerotilus natans | SEQ ID No. 15 | XV | 59.7 |
| | SEQ ID No. 16 adding 11 thymidine residues at 3' end (SEQ ID No. 33) | XVI | 50.9 |

Formation of DNA Chip

A DNA chip was formed by a microarray spot maker with pin having a diameter of 400 μm by spotting probes on a nylon membrane having positive charges (Roche, USA). The distance between the center of each two spots (probes) was 800 μm. The size of the chip was 0.45×0.50 cm² (5×6 spots). The probes listed in Table 3 were dissolved in a dye liquor (probe: dye liquor=1:1). The final concentration of the probe was 10 μM. The position of each probe is shown in FIG. 1. There are 30 spots in the FIG. 1. I-XVI indicate each probe listed in Table 3. M indicates position marker, PC indicates positive control probe, and NC indicates negative control (dye liquor only).

The formulation of the dye liquor was 10 ml of dye liquor containing 3 ml of 100% glycerol, 3 ml of bromophenol blue (per ml containing 5 mg of bromophenol blue, which was dissolved completely and filtered), 4 ml of 100% dimethyl sulfoxide, 20 μl of disodium ethylenediaminetraacetate (EDTA, 500 mM) and 0.1 ml of Tris-HCl (1 M, pH 7.5).

The sequence of the positive probe was 5' GGGT-GAAGTCGTAACAAGGTAGCCGTAttttttttt 3' (SEQ ID No. 18) (in 16A rDNA) (final concentration: 2.5 μM) and 9 position markers were 5'-digoxygenin-labeled ITS4 (TC-CTCCGCTTATTGATATGC) (SEQ ID No. 17) (final concentration: 0.1 µM).

After the DNA chip was completely formed, the DNA chip was dried in air and irradiated by a shortwave UV (Stratalinker 1800; Stratagen, La Jolla, Calif.) with an energy of 3 W/cm² for 30 seconds to fix the probes on the DNA chip. Then the DNA chip was stored in a dark and dry place.

Amplification of the 16S-23S Ribosomal DNA Intergenic Spacer Region Sequence of the Filamentous Microorganisms which is to be Identified The DNA of filamentous microorganisms which are to be identified are extracted to perform PCR. The filamentous microorganisms which are to be identified are shown in Table 4. Each 50 µl of polymerase chain reaction solution contained 5 µl of template DNA, 5 µl of PCR buffer (10×), 0.15 mM of deoxyribonucleoside triphosphates (dNTP) (PROtech Technologies, Inc. PTM8014, Taipei, Taiwan), 1 µM of universal primers pair: 2F-DIG (5' TTGTA CACAC CGCCC GTA 3' (SEQ ID No. 19)) and 10R-DIG (5' TTCGC CTTTC CCTCA CGGTA 3' (SEQ ID No. 20)), and 1 U of Taq polymerase (ProZyme™ II, PROtech Technologies, Inc., Taipei, Taiwan). An aliquot (50 µl) of mineral oil was added on each reaction solution. The polymerase chain reaction condition was: 94° C., 3 minutes; 94° C., 1 minutes, 55° C., 1 minute, 72° C., 1.5 minutes (35 cycles); 72° C., 7 minutes (1 cycle).

TABLE 4

The filamentous microorganisms which is to be identified:

| Strain | No. |
|---|---|
| Leucothrix mucor | DSM 621 |
| Leucothrix mucor | DSM 2157 |
| Leptothrix sp. | LMG 9068 |
| Leptothrix sp. | LMG 9069 |
| Haliscomenobacter hydrossis | DSM 1100 |
| Nocardia sp. | BCRC 15149 |
| Nocardia sp. | BCRC 15708 |
| Nocardia sp. | BCRC 15709 |
| Nocardia amarae | BCRC 13728 |
| Nocardia amarae | DSM 43391 |
| Thiothrix sp. | DSM 12730 |
| Thiothrix eikelboomii | ATCC 49788 |
| Sphaerotilus natans | DSM 565 |
| Sphaerotilus natans | DSM 5675 |
| Sphaerotilus natans | BCRC 10775 |

Hybridization of the DNA Chip and the 16S-23S Ribosomal DNA Intergenic Spacer Region Sequence of the Filamentous Microorganisms Each chip was placed in a 0.5×SSC buffer [1×SSC buffer containing 0.15 M NaCl, 0.015 M sodium citrate and 0.1% sodium dodecyl sulfate (SDS)] on a shaker (60 rpm) at room temperature and washed for 3 times for 3 minutes each time to remove the dye liquor and the probes which were not fixed on the nylon membrane. Pre-hybridization of the DNA chips was performed with a hybridization solution (5×SSC buffer, 1% (w/v) blocking solution (Roche, Mannheim, Germany), 0.1% N-laurylsarcosine (Sigma) and 0.02% SDS) at room temperature on a shaker for 2 hours. PCR products of 16S-23S ribosomal DNA intergenic spacer region sequence of the filamentous microorganisms were heated at 95° C. for 5 minutes to allow the double helix DNA to loosen and form single stranded DNA which were immediately placed in ice to hold the single stranded form. Each pre-hybridized DNA chip was put in different wells of the 24-well cell culture plate, 10 µl of the PCR product (labeled with DIG) of the filamentous microorganism which is to be identified and 300 µl of hybridization solution were added into the well and the 24 well cell culture plate was put in a hybridization oven (Firstek Scientific, DHO-100, Taipei, Taiwan) at 50° C. and shaken to perform hybridization for 1.5 hours. Afterwards, the hybridization solution was removed from the well and each DNA chip was washed with a 0.25×SSC buffer [1×SSC buffer containing 0.15 M NaCl, 0.015 M sodium citrate and 0.1% sodium dodecyl sulfate (SDS)] at room temperature 4 separate times, each time for 5 minutes in order to wash out the PCR product which had not hybridized.

Then, a 1× blocking solution (Roche, Germany) was added into the well at room temperature and shaken for 1 hour. After that, anti-digoxygenin-AP Fab fragments (Roche 1093274, Germany) which were diluted by 2500 times with the blocking solution was added into the well at room temperature and incubated for 1 hour, and then the antibody solution was removed. Each DNA chip was washed at room temperature 3 separate times, for 15 minutes each time by maleic acid buffer (0.1 M maleic acid, 0.15 M NaCl, 0.3% (v/v) Tween 20, pH 7.5) to wash out any antibody which did not bind to the DIG. A detection buffer was added into the well (0.1 M Tris-HCl and 0.15 M NaCl, pH 9.5) at room temperature and shaken for 5 minutes and then the detection buffer was removed.

NBT/BCIP (nitroblue tetrazolium chloride/5-bromo-4-chloro-3-indolylphosphate) (Roche 1681451, Mannheim, Germany) was diluted with the detection buffer for 50 times and well mixed to form a mixture solution. The mixture solution was added on each DNA chip and reacted with each DNA chip at 37° C. for 30-60 minutes without light and shaking during the color reaction. After the color reaction was complete, each DNA chip was washed with sterilized water 4 separate times, for 5 minutes each time in order to wash out the remaining NBT/BCIP. The DNA chips with color reactions were put on a filter paper and put into an oven for drying. After that, 3000 dpi high resolution scanner (Umax Powerlook 3000, Taipei, Taiwan) was used to scan each DNA chip and store the image results.

Results of Hybridization (1) *Leucothrix mucor*

The results of hybridization showed that probes I and II on the DNA chip had excellent hybridization result for 2 strains of *Leucothrix mucor* and did not have a cross-reaction with other filamentous microorganism strains. Moreover, probe II had a better hybridization result. FIG. 2 (A) and (B) show the results of *Leucothrix mucor* DSM 621 and *Leucothrix mucor* DSM 2157 reacting with the probes on the DNA chip, respectively. Compared with FIG. 1, the two spots shown in FIG. 2 (A) and (B) are the results of the color reaction of probes I and II and there is no cross-reaction. Therefore, probes I and II can identify *Leucothrix mucor* accurately.

(2) *Leptothrix* sp.

The results of hybridization showed that probes III and IV on the DNA chip had excellent hybridization result for 2 strains of *Leucothrix mucor* and did not have a cross-reaction with other filamentous microorganism strains. FIG. 2 (C) and (D) show the results of *Leptothrix* sp. LMG 9068 and *Leptothrix* sp. LMG 9069 reacting with the probes on the DNA chip, respectively. Compared with FIG. 1, the two spots shown in FIG. 2 (C) and (D) are the results of the color reaction of probes III and IV and there is no cross-reaction. Therefore, probes III and IV can identify *Leptothrix* sp. accurately.

(3) *Haliscomenobacter hydrossis*

The results of hybridization showed that probes V and VI on the DNA chip had excellent hybridization result for *Haliscomenobacter hydrossis* and did not have a cross-reaction with other filamentous microorganism strains. Moreover, probe V had a better hybridization result. FIG. 2 (E) shows the result of *Haliscomenobacter hydrossis* DSM 1100 reacting with the probes on the DNA chip. Compared with FIG. 1, the two spots shown in FIG. 2 (E) is the result of the color reaction of probes V and VI and there is no cross-reaction. Therefore, probes V and VI can identify *Haliscomenobacter hydrossis* accurately.

(4) *Nocardia* sp.

The results of hybridization showed that probes VII and VIII on the DNA chip had excellent hybridization result for 3 strains of *Nocardia* sp. and did not have a cross-reaction with other filamentous microorganism strains. FIG. 2 (F)-(H) show the results of *Nocardia* sp. BCRC 15149, *Nocardia* sp. BCRC 15708 and *Nocardia* sp. BCRC 15709 reacting with the probes on the DNA chip, respectively. Compared with FIG. 1, the two spots shown in FIG. 2 (F)-(H) are the results of the color reaction of probes VII and VIII and there is no cross-reaction. Therefore, probes VII and VIII can identify *Nocardia* sp. accurately.

(5) *Nocardia amarae*

The results of hybridization showed that probes IX and X on the DNA chip had excellent hybridization result for 2 strains of *Nocardia amarae* and did not have a cross-reaction with other filamentous microorganism strains. Moreover, probe IX had a better hybridization result. FIG. 2 (I) and (J) show the results of *Nocardia amarae* BCRC 13728 and *Nocardia amarae* DSM 43391 reacting with the probes on the DNA chip, respectively. Compared with FIG. 1, the two spots shown in FIG. 2 (I) and (J) are the results of the color reaction of probes IX and X and there is no cross-reaction. Therefore, probes IX and X can identify *Nocardia amarae* accurately.

(6) *Thiothrix* sp.

The results of hybridization showed that probes XI and XII on the DNA chip had excellent hybridization result for *Thiothrix* sp. and did not have a cross-reaction with other filamentous microorganism strains. Moreover, probe XII had a better hybridization result. FIG. 2 (K) shows the result of *Thiothrix* sp. DSM 12730 reacting with the probes on the DNA chip. Compared with FIG. 1, the two spots shown in FIG. 2 (K) is the result of the color reaction of probes XI and XII and there is no cross-reaction. Therefore, probes XI and XII can identify *Thiothrix* sp. accurately.

(7) *Thiothrix eikelboomii*

The results of hybridization showed that probes XIII and XIV on the DNA chip had excellent hybridization result for *Thiothrix eikelboomii* and did not have a cross-reaction with other filamentous microorganism strains. Moreover, probe XIV had a better hybridization result. FIG. 2 (L) shows the result of *Thiothrix eikelboomii* ATCC 49788 reacting with the probes on the DNA chip. Compared with FIG. 1, the two spots shown in FIG. 2 (L) is the result of the color reaction of probes XIII and XIV and there is no cross-reaction. Therefore, probes XIII and XIV can identify *Thiothrix eikelboomii* accurately.

(8) *Sphaerotilus natans*

The results of hybridization showed that probes XV and XVI on the DNA chip had excellent hybridization result for 3 strains of *Sphaerotilus natans* and did not have a cross-reaction with other filamentous microorganism strains. Moreover, probe XVI had a better hybridization result. FIG. 2 (M)-(O) show the results of *Sphaerotilus natans* DSM 565, *Sphaerotilus natans* DSM 5675 and *Sphaerotilus natans* BCRC 10775 reacting with the probes on the DNA chip, respectively. Compared with FIG. 1, the two spots shown in FIG. 2 (M)-(O) are the results of the color reaction of probes XV and XVI and there is no cross-reaction. Therefore, probes XV and XVI can identify *Sphaerotilus natans* accurately.

Sensitivity and Specificity of the DNA Chip of the Invention

By using the DNA chip of the invention, 15 filamentous microorganism strains which were the target microorganisms were correctly identified; the DNA chip thus demonstrated 100% sensitivity. Furthermore, 65 non-filamentous microorganism strains which were not the target microorganisms of the DNA chip showed no hybridization signal at all; the DNA chip thus demonstrated 100% specificity. Table 5 shows the results of the PCR products of non-filamentous microorganism hybridized to the probes on the DNA chip of the invention.

TABLE 5

Results of the PCR products of non-filamentous microorganism hybridized to the probes on the DNA chip of the invention.

| Strain | No. | Number of bacteria which is to be tested | Number of bacteria which have cross-reaction with the DNA chip |
|---|---|---|---|
| *Acinetobacter baumannii* | BCRC 15884 | 1 | 0 |
| *Acinetobacter calcoaceticus* | LMG 1046 | 1 | 0 |
| *Acinetobacter* genomic species 3 | LMG 1035 | 1 | 0 |
| *Acinetobacter junii* | BCRC 14854 | 1 | 0 |
| *Acinetobacter* genomic species 9 | LMG 985 | 1 | 0 |
| *Acinetobacter* genomic species 13TU | BCRC 15417 | 1 | 0 |
| *Acinetobacter* genomic species 15TU | CCUG 26390 | 1 | 0 |
| *Acinetobacter lwoffii* | BCRC 14855 | 1 | 0 |
| *Alcaligenes faecalis* subdp. *faecalis* | BCRC 10828, ATCC 8748, ATCC 19018 | 3 | 0 |
| *A. xylosoxidans* subsp. *xylosoxidans* | BCRC 12839 | 1 | 0 |
| *Bacillus subtilis* | BCRC 10225, BCRC 10029, BCRC 10058 | 3 | 0 |
| *Branhamella catarrhalis* | BCRC 10628, BCRC 10629 | 2 | 0 |
| *Burkholderia cepacia* | BCRC 13208 | 1 | 0 |
| *Chryseobacterium indologenes* | ATCC 29897 | 1 | 0 |
| *Chryseobacterium meningosepticum* | ATCC 13254, ATCC 13255 | 2 | 0 |
| *Comamonas testosteroni* | BCRC 10956, BCRC 14822 | 2 | 0 |
| *Delftia acidovorans* | ATCC 17455, BCRC 14819 | 2 | 0 |
| *Eikenella corrodens* | BCRC 14415 | 1 | 0 |
| *Exiguobacterium auarantiacum* | BCRC 17392 | 1 | 0 |
| *Gordonia alkanivorans* | DSM 44462 | 1 | 0 |
| *Gordonia westfalica* | DSM 44215 | 1 | 0 |
| *Moraxella atlantae* | CCUG 31324 | 1 | 0 |
| *Moraxella bovis* | BCRC 11229 | 1 | 0 |
| *Moraxella canis* | LMG 11194, CCUG 2153 | 2 | 0 |
| *Moraxella caviae* | CCUG 355 | 1 | 0 |
| *Moraxella nonliquefaciens* | BCRC 11230$^T$, BCRC11071 | 2 | 0 |
| *Moraxella osloensis* | BCRC 10705T, LMG 9616 | 2 | 0 |

TABLE 5-continued

Results of the PCR products of non-filamentous microorganism hybridized to the probes on the DNA chip of the invention.

| Strain | No. | Number of bacteria which is to be tested | Number of bacteria which have cross-reaction with the DNA chip |
|---|---|---|---|
| Pseudomonas aeruginosa | ATCC 27853 | 1 | 0 |
| Pseudomonas alcaligenes | ATCC 55044 | 1 | 0 |
| Pseudomonas fluorescens | BCRC 10304, BCRC 13902, BCRC 14347 | 3 | 0 |
| Pseudomonas mendocina | ATCC 25412, BCRC 10458 | 2 | 0 |
| Pseudomonas pseudoalcaligenes | BCRC 11902 | 1 | 0 |
| Pseudomonas putida | BCRC 10459 | 1 | 0 |
| Pseudomonas stutzeri | ATCC 17588, BCRC 14821 | 2 | 0 |
| Ralstonia pickettii | BCRC 14093, BCRC 14820 | 2 | 0 |
| Rhodococcus erythropolis | CC-BC11 | 1 | 0 |
| Rhodococcus ruber | BCRC 13379 | 1 | 0 |
| Serratia marcescens | BCRC 12833, BCRC 11576, BCRC 15326 | 3 | 0 |
| Shewanella putrefaciens | ATCC 49138, BCRC 10596 | 2 | 0 |
| Sphingomonas paucimobilis | BCRC 13893, BCRC 13954 | 2 | 0 |
| Stenotrophomonas maltophilia | BCRC 10737, BCRC 12495, BCRC 14110 | 3 | 0 |
| Streptococcus pseudopneumoniae | CCUG48465, CCUG 48455 | 2 | 0 |
| Total number | | | 65 |

* ATCC: American Type Culture Collection, Manassa, Va., USA
BCRC, Bioresources Collection and Research Center, Hsinchu, Taiwan
CCUG, Culture Collection, University of Göteborg, Göteborg, Sweden
LMG, Laboratorium voor Microbiologie, Gent, Belgium
NCCB, The Netherlands Culture Collection of Bacteria, Utrecht, The Netherlands
DSMZ, Deutsche Sammlung von Mikroorganismen und Zellkulture, Braunschweig, Germany While the invention has been described by way of example and in terms of the embodiment, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An isolated oligonucleotide sequence for identifying *Leucothrix mucor*, comprising: SEQ ID No. 1, SEQ ID No. 2, the full complementary sequences thereof or derivatives thereof, wherein the derivative is 5' and/or 3' end of the sequence SEQ ID No. 1 or 2 with at least one thymidine residue added or is 5' and/or 3' end of the sequence SEQ ID No. 1 or 2 with one or two nucleotides added or deleted from its 5' and/or 3' end.

2. The oligonucleotide sequence for identifying *Leucothrix mucor* as claimed in claim 1, wherein *Leucothrix mucor* comprises *Leucothrix mucor* DSM 621 or *Leucothrix mucor* DSM 2157.

3. An isolated oligonucleotide sequence for identifying *Leptothrix* sp., comprising: SEQ ID No. 3, SEQ ID No. 4, the full complementary sequences thereof or derivatives thereof, wherein the derivative is 5' and/or 3' end of the sequence SEQ ID No. 3 or 4 with at least one thymidine residue added or is 5' and/or 3' end of the sequence SEQ ID No. 3 or 4 with one or two nucleotides added or deleted and *Leptothrix* sp. comprises *Leptothrix* sp. LMG 9068 or *Leptothrix* sp. LMG 9069 from its 5' and/or 3' end.

4. An isolated oligonucleotide sequence for identifying *Haliscomenobacter hydrossis*, comprising: SEQ ID No. 5, SEQ ID No. 6, the full complementary sequences thereof or derivatives thereof, wherein the derivative is 5' and/or 3' end of the sequence SEQ ID No. 5 or 6 with at least one thymidine residue added or is 5' and/or 3' end of the sequence SEQ ID No. 5 or 6 with one or two nucleotides added or deleted from its 5' and/or 3' end.

5. The oligonucleotide sequence for identifying *Haliscomenobacter hydrossis* as claimed in claim 4, wherein *Haliscomenobacter hydrossis* comprises *Haliscomenobacter hydrossis* DSM 1100.

6. An isolated oligonucleotide sequence for identifying *Nocardia amarae*, comprising: SEQ ID No. 9, SEQ ID No. 10, the full complementary sequences thereof or derivatives thereof, wherein the derivative is 5' and/or 3' end of the sequence SEQ ID No. 9 or 10 with at least one thymidine residue added or is 5' and/or 3' end of the sequence SEQ ID No. 9 or 10 with one or two nucleotides added or deleted from its 5' and/or 3' end.

7. The oligonucleotide sequence for identifying *Nocardia amarae* as claimed in claim 6, wherein *Nocardia amarae* comprises *Nocardia amarae* BCRC 13728 or *Nocardia amarae* DSM 43391.

8. An isolated oligonucleotide sequence for identifying *Thiothrix* sp., comprising: SEQ ID No. 11, SEQ ID No. 12, the full complementary sequences thereof or derivatives thereof, wherein the derivative is 5' and/or 3' end of the sequence SEQ ID No. 11 or 12 with at least one thymidine residue added or is 5' and/or 3' end of the sequence SEQ ID No. 11 or 12 with one or two nucleotides added or deleted and *Thiothrix* sp. comprises *Thiothrix* sp. DSM 12730 from its 5' and/or 3' end.

9. An isolated oligonucleotide sequence for identifying *Thiothrix eikelboomii*, comprising: SEQ ID No. 13, SEQ ID No. 14, the full complementary sequences thereof or derivatives thereof, wherein the derivative is 5' and/or 3' end of the sequence SEQ ID No. 13 or 14 with at least one thymidine residue added or is 5' and/or 3' end of the sequence SEQ ID No. 13 or 14 with one or two nucleotides added or deleted from its 5' and/or 3' end.

10. The oligonucleotide sequence for identifying *Thiothrix eikelboomii* as claimed in claim 9, wherein *Thiothrix eikelboomii* comprises *Thiothrix eikelboomii* ATCC 49788.

11. An isolated oligonucleotide sequence for identifying *Sphaerotilus natans*, comprising: SEQ ID No. 15, SEQ ID No. 16, the full complementary sequences thereof or derivatives thereof, wherein the derivative is 5' and/or 3' end of the sequence SEQ ID No. 15 or 16 with at least one thymidine residue added or is 5' and/or 3' end of the sequence SEQ ID No. 15 or 16 with one or two nucleotides added or deleted from its 5' and/or 3' end.

12. The oligonucleotide sequence for identifying *Sphaerotilus natans* as claimed in claim 9, wherein *Sphaerotilus natans* comprises *Sphaerotilus natans* DSM 565, *Sphaerotilus natans* DSM 5675 or *Sphaerotilus natans* BCRC 10775.

13. A DNA chip for identifying filamentous microorganisms, including a substrate and a plurality of probes, wherein the probe comprises SEQ ID No. 1, 2, 3, 4, 5, 6, 9, 10, 11, 12, 13, 14, 15, 16, complementary sequences thereof, derivatives thereof or combinations thereof, and wherein the derivative is SEQ ID No. 1, 2, 3, 4, 5, 6, 9, 10, 11, 12, 13, 14, 15 or 16 with at least one thymidine residue added to its 5' and/or 3' end, or is SEQ ID No. 1, 2, 3, 4, 5, 6, 9, 10, 11, 12, 13, 14, 15 or 16 with one or two nucleotides added to or deleted from its 5' and/or 3' end.

14. The DNA chip for identifying filamentous microorganisms as claimed in claim 13, wherein a number of the thymidine residue is 5-15.

15. The DNA chip for identifying filamentous microorganisms as claimed in claim 13, wherein SEQ ID No. 1, SEQ ID No. 2, the complementary sequences thereof and/or derivatives thereof are/is for identifying *Leucothrix mucor*.

16. The DNA chip for identifying filamentous microorganisms as claimed in claim 13, wherein SEQ ID No. 3, SEQ ID No. 4, the complementary sequences thereof and/or derivatives thereof are/is for identifying *Leucothrix* sp. and *Leucothrix* sp. comprises *Leptothrix* sp. LMG 9068 and *Leptothrix* sp. LMG 9069.

17. The DNA chip for identifying filamentous microorganisms as claimed in claim 13, wherein SEQ ID No. 5, SEQ ID No. 6, the complementary sequences thereof and/or derivatives thereof are/is for identifying *Haliscomenobacter hydrossis*.

18. The DNA chip for identifying filamentous microorganisms as claimed in claim 13, wherein SEQ ID No. 9, SEQ ID No. 10, the complementary sequences thereof and/or derivatives thereof are/is for identifying *Nocardia amarae*.

19. The DNA chip for identifying filamentous microorganisms as claimed in claim 13, wherein SEQ ID No. 11, SEQ ID No. 12, the complementary sequences thereof and/or derivatives thereof are/is for identifying *Thiothrix* sp. and *Thiothrix* sp. comprises *Thiothrix* sp. DSM 12730.

20. The DNA chip for identifying filamentous microorganisms as claimed in claim 13, wherein SEQ ID No. 13, SEQ ID No. 14, the complementary sequences thereof and/or derivatives thereof are/is for identifying *Thiothrix eikelboomii*.

21. The DNA chip for identifying filamentous microorganisms as claimed in claim 13, wherein SEQ ID No. 15, SEQ ID No. 16, the complementary sequences thereof and/or derivatives thereof are/is for identifying *Sphaerotilus natans*.

22. The DNA chip for identifying filamentous microorganisms as claimed in claim 13, wherein the substrate comprises nylon membrane, glass, cellulose nitrate membrane or plastic.

23. A method for identifying filamentous microorganisms causing sludge bulking, comprising:
(a) extracting a DNA having a 16S-23S ribosomal DNA intergenic spacer region sequence of a filamentous microorganism which is to be identified;

(b) amplifying the 16S-23S ribosomal DNA intergenic spacer region sequence by a pair of universal primers (c) letting the 16S-23S ribosomal DNA intergenic spacer region sequence amplified in step (b) hybridize with the DNA chip of claim 13 for identifying filamentous microorganisms claimed in claim 13; and (d) observing which probe of the DNA chip the 16S-23S ribosomal DNA intergenic spacer region sequence amplified in step (b) is hybridized with to identify the microorganism which is to be identified.

* * * * *